United States Patent
Norton et al.

(10) Patent No.: US 7,917,217 B2
(45) Date of Patent: Mar. 29, 2011

(54) WET TANTALUM REFORMATION METHOD AND APPARATUS

(75) Inventors: John D. Norton, Minneapolis, MN (US); Brian J. Melody, Greer, SC (US); John Tony Kinard, Greer, SC (US)

(73) Assignees: Medtronic, Inc., Minneapolis, MN (US); Kemet Electronics Corporation, Simpsonville, SC (US)

( * ) Notice: Subject to any disclaimer, the term of this patent is extended or adjusted under 35 U.S.C. 154(b) by 325 days.

(21) Appl. No.: 10/431,356

(22) Filed: May 7, 2003

(65) Prior Publication Data

US 2004/0225327 A1    Nov. 11, 2004

(51) Int. Cl.
*A61N 1/00* (2006.01)

(52) U.S. Cl. ......................................................... 607/36

(58) Field of Classification Search ................. 607/1–5, 607/36; 323/242; 420/427; 361/502; 29/25.41
See application file for complete search history.

(56) References Cited

U.S. PATENT DOCUMENTS

| | | | |
|---|---|---|---|
| 2,965,690 A * | 12/1960 | Petersen et al. | 361/505 |
| 3,684,947 A * | 8/1972 | Evalds et al. | 323/242 |
| 3,850,764 A * | 11/1974 | Herczog et al. | 29/25.41 |
| 4,645,533 A * | 2/1987 | Izumi | 420/427 |
| 4,693,253 A | 9/1987 | Adams | |
| 4,780,797 A | 10/1988 | Libby | |
| 4,830,006 A | 5/1989 | Haluska et al. | |
| 4,942,500 A | 7/1990 | Libby et al. | |
| 4,971,058 A | 11/1990 | Pless et al. | |
| 5,043,849 A | 8/1991 | Libby | |
| 5,098,485 A | 3/1992 | Evans | |
| 5,265,588 A | 11/1993 | Nelson et al. | |
| 5,312,439 A | 5/1994 | Loeb | |
| 5,312,441 A | 5/1994 | Mader et al. | |
| 5,369,547 A | 11/1994 | Evans | |
| 5,469,325 A | 11/1995 | Evans | |
| 5,559,667 A | 9/1996 | Evans | |
| 5,737,181 A | 4/1998 | Evans | |
| 5,754,394 A | 5/1998 | Evans et al. | |
| 5,827,326 A | 10/1998 | Kroll et al. | |
| 5,851,506 A | 12/1998 | Zheng et al. | |
| 5,861,006 A | 1/1999 | Kroll | |
| 5,894,403 A | 4/1999 | Shah et al. | |
| 5,899,923 A | 5/1999 | Kroll et al. | |
| 5,982,609 A | 11/1999 | Evans | |
| 5,999,852 A | 12/1999 | Elabbady et al. | |
| 6,005,370 A | 12/1999 | Gustavson et al. | |

(Continued)

FOREIGN PATENT DOCUMENTS

DE    198 36 651 A1    2/2000

(Continued)

OTHER PUBLICATIONS

PCT International Search Report based on PCT/US2004/014037, date of mailing of the International Search Report—Sep. 11, 2004, 4 total pgs.

(Continued)

*Primary Examiner* — George Manuel

(57) ABSTRACT

A method of reforming a wet-tantalum capacitor is disclosed. The method comprises charging the capacitor to a voltage that is substantially less than one of a maximum and rated voltage for the capacitor. The method also comprises providing an open circuit condition and allowing the capacitor to at least partially discharge through leakage current.

39 Claims, 6 Drawing Sheets

U.S. PATENT DOCUMENTS

| | | | |
|---|---|---|---|
| 6,094,597 | A | 7/2000 | Wold |
| 6,096,062 | A | 8/2000 | Silvian |
| 6,136,176 | A | 10/2000 | Wheeler et al. |
| 6,208,502 | B1 | 3/2001 | Hudis et al. |
| 6,283,985 | B1 * | 9/2001 | Harguth et al. ............ 607/1 |
| 7,131,988 | B2 * | 11/2006 | Harguth et al. ............ 607/1 |
| 2001/0047190 | A1 | 11/2001 | Harguth et al. |
| 2002/0095186 | A1 | 7/2002 | Harguth et al. |
| 2003/0088273 | A1 | 5/2003 | Liu et al. |
| 2003/0090857 | A1 * | 5/2003 | Liu et al. ............ 361/502 |

FOREIGN PATENT DOCUMENTS

| | | |
|---|---|---|
| EP | 1 267 111 A1 | 12/2002 |
| EP | 1 312 390 A2 | 5/2003 |
| WO | WO 00/02213 A1 | 1/2000 |
| WO | WO 01/73801 | 10/2001 |
| WO | WO 2004/102639 A2 | 11/2004 |

OTHER PUBLICATIONS

B.E. Conway, "Electrochemical Supercapacitors", 58 pages, Kluwer Academic Publishers (1999).

G.E. Loeb, C.J. Zamin, J.H. Schulman, P.R. Troyk Injectable microstimulator for functional electrical stimulation, 7 pages, Med. & Biol. Eng. & Comput., 29, NSI3-NS19 (1991).

I. D. Raistrick, "Electrochemical capacitors", in "Electrochemistry of semiconductors and electronics—processes and devices", 30 pages, eds: John McHardy and Frank Ludwig, Noyes Publications (1992).

S. Trasatti (ed), "Electrodes of conductive metallic oxides", part A, 59 pages, Elesevier (1980).

S. Trasatti, G. Buzzanca, "Ruthenium dioxide: a new and interesting electrode material. Solid state structure and electrochemical behavior," 5 pages, Journal of Electroanalytical Chemistry and Interfacial Electrochemistry, 29, App. 1-5, (1971).

Written Opinion for PCT/US2004/014037, mail date Jan. 12, 2004, 6 pages.

Translation of the reasoning of Official Action for Japanese Patent Application 2006-532797, dated Feb. 19, 2010, 2 pages.

Communication pursuant to Article 94(3) EPC for Application No. 04 751 431.0—2214, dated Dec. 14, 2009, 5 pages.

Office Action for U.S. Appl. No. 11/932,235, mail date Sep. 20, 2010, 4 pages.

Response to Office Action for U.S. Appl. No. 11/932,235, Dec. 20, 2010, 8 pages.

Office Action for U.S. Appl. No. 11/932,235, mail date Jan. 12, 2011, 4 pages.

European Patent Office Action for Application No. 04751431.0, mail date Dec. 14, 2009, 5 pages.

Response to European Application No. 04751431.0, Jun. 23, 2010, 4 pages.

Response to Office Action for Japanese Patent Application No. 2006-532797, Aug. 19, 2010, 4 pages.

PCT International Search Report for PCT/US2004/014037, Nov. 25, 2004, 5 pages.

PCT International Preliminary Report on Patentability and Written Opinion for PCT/US2004/014037, mail date Nov. 24, 2005, 7 pages.

* cited by examiner

WET TANTALUM REFORMATION METHOD AND APPARATUS

CROSS-REFERENCE TO RELATED PATENT APPLICATIONS

This application is related to U.S. application Ser. No. 10/261,066, entitled "METHOD AND APPARATUS FOR MAINTAINING ENERGY STORAGE IN AN ELECTRICAL STORAGE DEVICE", filed Sep. 30, 2002, and which is herein incorporated by reference.

BACKGROUND OF THE INVENTION

The present invention relates generally to the field of capacitors. More specifically, the present invention relates to wet-tantalum capacitors for use in medical devices (e.g., implantable medical devices (IMDs)) or other types of devices.

Since their earliest inception, there has been significant advancement in body-implantable electronic medical devices. Today, these implantable devices include therapeutic and diagnostic devices, such as pacemakers, cardioverters, defibrillators, neural stimulators, drug administering devices, among others for alleviating the adverse effects of various health ailments. Conventional implantable medical devices are also vastly more sophisticated and complex than their predecessors, and are therefore capable of performing considerably more complex tasks for reducing the effects of the health ailments they were designed to treat.

Usually, body-implantable medical devices rely on battery power to perform their therapeutic and/or diagnostic tasks. The battery supplies power to the electrical components of the implantable medical device, and also typically provides power to a capacitor of, for example, a defibrillator device, which stores the energy supplied thereto from the battery. The capacitor typically includes an anode, a cathode, and a fluid electrolyte disposed between the anode and cathode. The various types of materials used for the anode, cathode, and electrolyte may have an impact on the capacitor's ability to store energy from the battery, and the rate at which the energy is stored prior to discharging the capacitor. Importantly, the materials may also affect the volume of the device. Smaller defibrillator devices, which in turn require smaller capacitors, will typically enhance the patient's comfort.

Typically, in an implantable medical device, the capacitor is used to deliver therapeutic electric signals to the patient's heart in response to the device receiving abnormal feedback signals from the heart. The therapeutic electric signals delivered to the patient's heart may vary somewhat in intensity depending on the patients' physiology and the details of the implant. Typically, the therapeutic electric pulse energy delivered to the heart is on the order of 30 J for a single defibrillation pulse. The energy stored in the capacitor has to be somewhat larger due to losses along the delivery path during the release of the energy.

The capacitor, therefore, plays a vital role in the implantable defibrillator device for if the energy supplied from the battery is not stored in a timely manner within the capacitor prior to its therapeutic discharge or if the energy is not released in a timely manner during its therapeutic delivery, the capacitor may not be able to deliver sufficient energy to the patient's heart at a critical point in time when deemed necessary by the implantable medical device. As a result, the performance of the medical device may be adversely affected by the capacitor's inability to adequately and/or quickly store the energy supplied by the battery.

Wet-tantalum capacitors use tantalum and tantalum oxide ($Ta_2O_5$) instead of the conventional aluminum and aluminum oxide in aluminum electrolytic capacitors. Wet-tantalum capacitors typically include a tantalum metal anode, a tantalum oxide dielectric combined with a liquid electrolyte that is sandwiched between the anode and a cathode. The cathode may be a tantalum metal using a $Ta_2O_5$ dielectric or other material, for example, $RuO_2$.

An exemplary wet-tantalum capacitor may comprise a tantalum metal anode, $Ta_2O_5$ dielectric, a liquid electrolyte, and a cathode of material other than tantalum, for example, $RuO_2$. Capacitors of this description are known in the trade as hybrid capacitors, with some versions having tantalum cases and others having polypropylene cases. See also U.S. Pat. Nos. 5,982,609; 5,469,325; 5,737,181; and 5,754,394.

Exemplary specifications for the wet-tantalum capacitors are 185 volts surge, 60 microamp leakage current at 175 volts, 90 microamp leakage current at 185 volts, an AC capacitance of 490 microfarads, and equivalent series resistance (ESR) of 1.2 Ohms. Capacitors meeting these specifications or having similar construction are manufactured by Wilson Greatbatch Technologies of Clarence, N.Y. or Evans Capacitor Company of East Providence, R.I.

A maintenance issue exists for wet-tantalum capacitors, which is that their charging efficiency degrades over long periods of inactivity. The degraded charging efficiency stems from hydration of either the tantalum-oxide dielectric and/or hydration of a sparingly soluble phosphate that is deposited within the interstices of the anode during formation of the anodic oxide. This hydration problem leads to degraded charging efficiency and thereby requires the device battery to expend more energy to charge the capacitor for future use in providing therapy.

Previous attempts at solving the problem of deformation require that the capacitor be charged to a voltage at or near the rated voltage of the capacitor for a period of time and then discharging either through a non-therapeutic load or through leakage currents. In U.S. Pat. No. 6,283,985, Harguth, et al. state they have discovered the need for reforming wet-tantalum capacitors in an implantable cardioverter defibrillator (ICD) and describe a method for doing so, albeit contrary to and without the advantages of the methods and apparatuses described herein.

Accordingly, there is a need for an efficient reformation method and apparatus for wet-tantalum capacitors. Further, there is a need for a method and apparatus for reforming wet-tantalum capacitors which require reduced amounts of energy from a power source. Further still, there is a need for wet-tantalum capacitors which provide improved reformation properties when compared with conventional wet-tantalum capacitor reformation techniques. Yet further still, there is a need for a method and apparatus for reforming wet-tantalum capacitors which addresses the underlying mechanisms that lead to the degradation of wet-tantalum capacitor performance.

It would be desirable to provide a system and/or method that provides one or more of these or other advantageous features. Other features and advantages will be made apparent from the present specification. The teachings disclosed extend to those embodiments which fall within the scope of the appended claims, regardless of whether they accomplish one or more of the aforementioned needs.

SUMMARY OF THE INVENTION

An exemplary embodiment of the invention relates to a method of reforming a wet-tantalum capacitor. The method comprises charging the capacitor to a voltage that is substantially less than one of a maximum and rated voltage for the capacitor. The method also comprises providing an open circuit condition and allowing the capacitor to at least partially discharge through leakage current.

Another exemplary embodiment of the invention relates to a method of reforming a wet-tantalum capacitor. The method comprises charging the capacitor to a voltage that is substantially less than a rated voltage for the capacitor. The method also comprises discharging the capacitor through a non-therapeutic load.

Yet another exemplary embodiment of the invention relates to a method of reforming a wet-tantalum capacitor. The method comprises applying an electric field across the capacitor dielectric. The method also comprises causing dehydration of an anodic oxide phosphate deposit.

Yet still another exemplary embodiment of the invention relates to a method of reducing the size of an implantable cardiac defibrillator. The method comprises reducing the size of the battery powering the defibrillator, by reducing power requirements in reforming the capacitor, wherein reforming the capacitor is accomplished by, charging the capacitor to a voltage that is substantially less than a rated voltage for the capacitor, and providing a condition by which the capacitor is discharged.

Yet still another exemplary embodiment of the invention relates to an implantable cardiac device. The implantable cardiac device includes a processing device for controlling the implantable cardiac device. The processing device comprises a processor, a power source, and a capacitor device including at least one wet-tantalum capacitor, the device coupled to the power source wherein the processor carries out instructions to charge the at least one wet-tantalum capacitor to a voltage that is substantially less than a rated voltage for the at least one wet-tantalum capacitor and to discharge the at least one wet-tantalum capacitor by at least one of opening the circuit to allow for current leakage and/or providing a path for a non-therapeutic discharge.

Yet still another exemplary embodiment of the invention relates to a program storage device readable by a machine, tangibly embodying a program of instructions executable by the machine to perform method steps for reforming a wet-tantalum capacitor. The method comprises charging the capacitor to a voltage that is substantially less than a rated voltage for the capacitor. The method also comprises providing a condition by which the capacitor is discharged.

Yet still another exemplary embodiment of the invention relates to an apparatus for reforming a wet-tantalum capacitor. The apparatus comprises a means for charging the capacitor to a voltage that is substantially less than a rated voltage for the capacitor. The apparatus also comprises a means for providing a condition by which the capacitor is discharged.

Alternative examples and other exemplary embodiments relate to other features and combination of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION OF THE PREFERRED EMBODIMENTS

Figure 1:
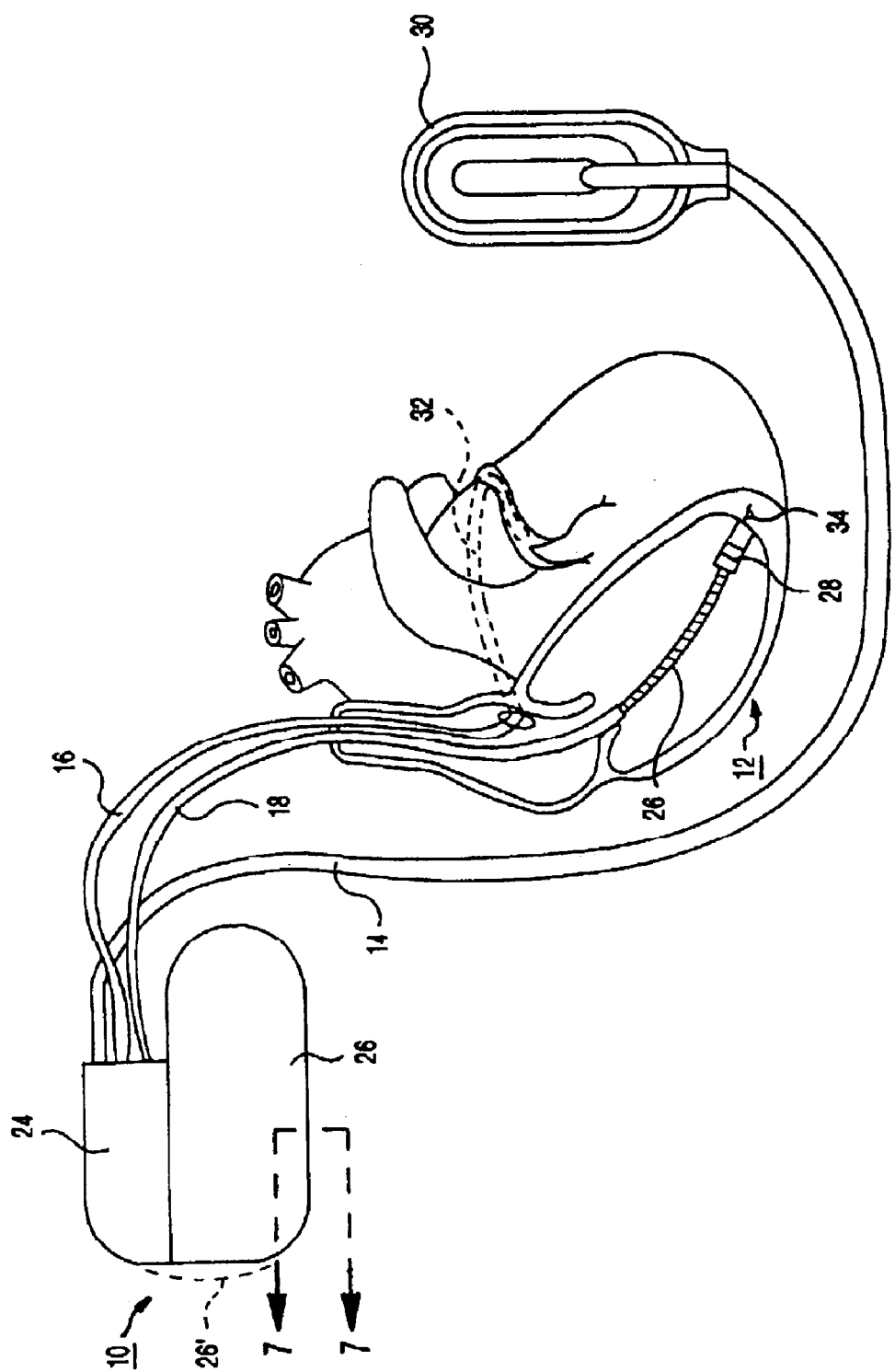
FIG. 1 illustrates exemplary physical components of an ICD and lead system extending to the heart of the type in which the invention may be advantageously practiced.

Before describing in detail the particular improved system and method, it should be observed that the invention includes, but is not limited to a novel structural combination of conventional electronic processing components and circuits, and not in the particular detailed configurations thereof. Accordingly, the structure, methods, functions, control and arrangement of conventional components and circuits have, for the most part, been illustrated in the drawings by readily understandable block representations and schematic diagrams, in order not to obscure the disclosure with structural details which will be readily apparent to those skilled in the art, having the benefit of the description herein. Further, the invention is not limited to the particular embodiments depicted in the exemplary diagrams, but should be construed in accordance with the language in the claims.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The invention can be implemented in any implantable medical device (IMD) requiring a transformer for providing a therapy and/or monitoring function such as described in U.S. Pat. No. 6,094,597, herein incorporated by reference. The invention will be described in relation to an ICD operating system design, but it is not intended that the invention be limited to that particular application when it can be advantageously implemented in other ICD systems and in other IMDs.

Such ICD typically are formed having a housing that is hermetically sealed and, therefore, is impervious to body fluids, and a connector header for making electrical and mechanical connection with one or more leads bearing pacing, sensing and cardioversion/defibrillation electrodes adapted to be located in or around selected chambers of the heart. The housing is typically formed of a suitable, body-compatible material approved for medical use, such as titanium and is shaped physiologically so as to avoid sharp edges which might lead to tissue necrosis following implantation. Typically, the housing is formed having major opposed or parallel surfaces joined together by sides enclosing an interior housing chamber or cavity and having electrical feed-throughs extending therethrough and into the connector header. The housing cavity receives the battery(s) and the high voltage (HV) and low voltage (LV) electronic circuitry which can comprise ICs, hybrid circuits and discrete components, e.g., but not limited to, the step-up transformer and the high voltage output capacitor(s). Although, there is no particular preferred embodiment of such an ICD, FIGS. 1 and 2 depict one form of such an ICD in which the present invention can be advantageously implemented.

Figure 2:
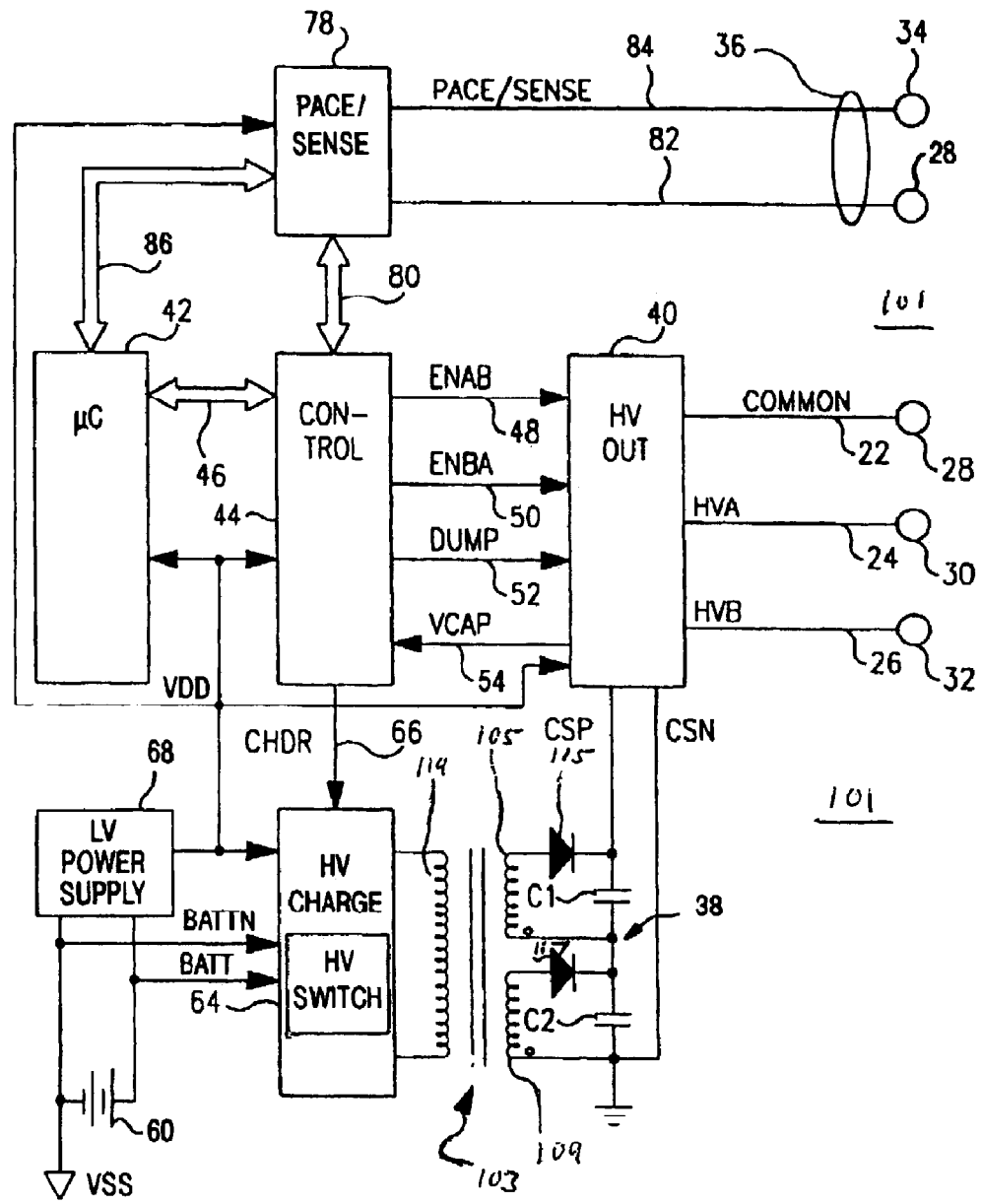
FIG. 2 is a functional block diagram illustrating a prior art ICD system having a conventional high voltage, single core, step-up transformer which can be advantageously modified to employ the capacitor reformation technique described.

In FIG. 1, an ICD 10 and associated 14, 16 and 18 are illustrated in relation to a patient's heart 12 as in FIG. 1 of U.S. Pat. No. 5,265,588, incorporated herein by reference. The ICD 10 comprises the hermetically sealed, metallic housing 36 and a multi-lumen connector header 24 which contains separate connector blocks and ports for receiving and electrically and mechanically attaching the proximal connector ends of the leads 14, 16 and 18. The feed-throughs (not shown) extend from the connector blocks (not shown) within the connector header 24 and the internal high voltage and low voltage circuitry within the housing 22 in a manner well known in the art.

The cardioversion/defibrillation leads 14, 16 and 18 bear relatively large surface area cardioversion/defibrillation electrodes 30, 32 and 26, respectively that are located in, on or about the heart 12. Cardioversion/defibrillation lead 14 extends subcutaneously and terminates distally in a subcutaneous electrode 30, which is intended to be mounted subcutaneously in the region of the left chest. Cardioversion/defibrillation lead 16 extends transvenously and terminates distally in an elongated coil CS electrode 32 which is located in the coronary sinus and great vein region of the heart 12 and extends around the heart from a point within the opening of the coronary sinus to a point in the vicinity of the left atrial appendage. Ventricular cardioversion/defibrillation lead 18 extends transvenously and is provided with an elongated electrode coil 26 which is located in the right ventricular chamber of the heart 12. Cardioversion/defibrillation therapeutic discharges can be applied between selected cardioversion/defibrillation electrodes.

The ICD 10 preferably further incorporates atrial and/or ventricular EGM sensing capabilities for detecting atrial and/or ventricular arrhythmias and optionally providing therapy for atrial and/or ventricular arrhythmias. Ventricular lead 18 also includes a ventricular pace/sense electrode 34 which takes the form of a helical coil which is screwed into the myocardial tissue of the right ventricle. Lead 18 may also include an additional pace/sense electrode 28 for near field ventricular EGM sensing or a surface electrode on the ICD 10 may be paired with the helical coil electrode 34 for far field ventricular EGM sensing. Additional near field and/or far field atrial EGM sensing and atrial pacing capabilities can be provided using atrial pace/sense electrode pairs on the atrial lead 16 and/or the IPG 10. The invention is also believed workable in the context of multiple lead and electrode systems appropriate for the treatment of the patient's arrhythmias.

In the system illustrated, ventricular cardiac pacing pulses are delivered between helical pace/sense electrode 34 and ring electrode 28. Pace/sense electrodes 28 and 34 are also employed to sense EGM signals characteristic of ventricular contractions. As illustrated, it is anticipated that the right ventricular cardioversion/defibrillation electrode 26 will serve as the common electrode during sequential and simultaneous pulse multiple electrode defibrillation regimens. For example, during a simultaneous pulse defibrillation regimen, high voltage therapeutic discharges would simultaneously be delivered between cardioversion/defibrillation electrodes 26 and 30 and between cardioversion/defibrillation electrodes 26 and 32. During sequential pulse defibrillation, it is envisioned that high voltage therapeutic discharges would be delivered sequentially between cardioversion/defibrillation electrodes 30 and 26 and between coronary sinus cardioversion/defibrillation electrode 32 and right ventricular cardioversion/defibrillation electrode 26. Single pulse, two electrode defibrillation pulse regimens may be also provided, typically between right ventricular cardioversion/defibrillation electrode 26 and coronary sinus cardioversion/defibrillation electrode 32. Alternatively, single pulses may be delivered between cardioversion/defibrillation electrodes 28 and 30. The particular interconnection of the cardioversion/defibrillation on electrodes to the ICD will depend somewhat on which specific cardioversion/defibrillation pulse regimen is employed.

FIG. 2 is a block diagram illustrating a prior art ICD system 101 having a conventional high voltage, single core, step-up transformer 103. The ICD system 101 is merely exemplary of a variety of single chamber and dual chamber ICD systems having all or some of the capabilities described above in which the invention can be implemented. The exemplary ICD system 101 includes a HV battery 60, a DC-DC converter comprising a high voltage ((HV) charging circuit 64, a HV single core transformer, a HV output capacitor bank 38, and a HV output or discharge circuit 40 for discharging the charge on the HV output capacitor bank 38. The charge on the HV output capacitor bank 38, comprising series connected wet-tantalum capacitors C1 and C2 in this case, is selectively discharged through the cardioversion/defibrillation electrodes 26, 30 and 32 coupled via leads 22, 24 and 26 to the HV out circuitry 40. Similar ICD systems to that depicted in FIG. 2 in which the present invention can be implemented are shown, for example, in U.S. Pat. Nos. 4,830,006, 4,693,253, 4,971,058, 5,312,441, and 5,827,326, all incorporated herein by reference in their entireties, for example.

The exemplary prior art ICD system 101 of FIG. 2 is powered by the battery 60 coupled to the HV charging circuit 64 and to a power supply 68 which provides regulated power to the LV ICs, hybrid circuits, and discrete components of the system 101. Preferably, battery 60 is a lithium silver vanadium battery that can be employed to provide the HV capacitor charging current and that produces a voltage from about 3.2 volts when fresh to about 2.5 volts at specified end of service for a single chamber ICD and twice these values for a dual chamber ICD.

The LV ICs and hybrid circuits powered by supply voltage VDD (and other regulated voltages generated by LV power supply 68 in certain instances) comprise at least the illustrated microcomputer 42, the control and logic circuitry 44, and the pace/sense circuitry 78, and may include other circuits, e.g., a system clock, power-on-reset circuitry, telemetry circuitry, physiologic and activity sensing circuitry etc. The LV supply voltage VDD is also applied to the HV charging circuit 64 to power the DC-DC conversion switching circuits and to the HV output circuit 40 to power operation of certain circuitry therein.

As illustrated, the ICD system 101 is controlled by the operation of the microcomputer 42 and control circuitry 44 following an operating program stored in ROM and RAM which performs all necessary computational and control functions. Microcomputer 42 is linked to control circuitry 44 by means of a bi-directional data/control bus 46 and further interrupt and signal lines (not shown), and thereby controls operation of the HV output circuitry 40 and the HV charging circuitry 64. Pace/sense circuitry 78 awakens microcomputer 42 to perform any necessary mathematical calculations, to perform tachycardia and fibrillation detection procedures and to update the time intervals controlled by the timers in pace/sense circuitry 78 and control circuitry 44 upon receipt of a reprogramming command or on the occurrence of signals indicative of delivery of cardiac pacing pulses or the sensing of selected features of the EGM characteristic of cardiac contractions. The basic operation of such a system in the context of an implantable pacemaker/cardioverter/defibrillator may correspond to any of the systems known to the art, and in more particular may correspond generally to those illustrated in the above-incorporated '006, '253, and '441 patents for example.

Pace/sense circuitry 78 includes an R-wave sense amplifier according to the prior art as described in the above-incorporated '588 patent. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microcomputer 42 via control/data bus 86. Control signals triggering generation of cardiac pacing pulses by pace/sense circuitry 78 and signals indicative of the occurrence of R-waves from pace/sense circuitry 78 are communicated to control circuitry 44 by means of a bidirectional data bus 80. Pace/sense circuitry 78 is also coupled to ventricular pace/sense electrodes 28 and 34, illustrated in FIG. 1, by means of a conductors 82 and 84 in ventricular lead 36, allowing for bipolar sensing of R-waves and for delivery of bipolar pacing pulses to the ventricle of the heart 12. As noted above, dual chamber or single chamber atrial pacing and sensing functions can also or alternatively be provided employing suitable pace/sense circuitry 78 and suitable far field (unipolar) or near field (bipolar) atrial electrode pairs.

In this illustrated embodiment, the HV output circuitry 40 is coupled to the output capacitor bank 38, including capacitors C1 and C2, and is programmable for delivering biphasic cardioversion/defibrillation shocks to selected cardioversion/defibrillation electrodes. The output capacitors C1 and C2 are coupled to secondary windings 105 and 109 of step-up transformer 103 by means of the diodes 115 and 117. The primary winding 119 of step-up transformer 103 is coupled to the HV charging circuitry 64. The HV charging circuitry 64 is controlled by the CHDR signal on line 66 supplied by control circuitry 44 when a malignant arrhythmia subject to cardioversion/defibrillation therapy is detected. The output capacitors C1 and C2 are charged by oscillations of the high frequency, HV transformer 103 in the manner disclosed in detail in the above-incorporate '588 patent. The CSP and CSN voltage across the capacitor bank 38 is monitored and applied via the VCAP signal on line 54 to the control circuitry which detects the point when the VCAP signal level matches the programmed energy level of the cardioversion/defibrillation high voltage therapeutic discharge to be delivered. When that condition is satisfied, the control circuitry 44 terminates the CHDR signal and commences the operations to deliver the biphasic cardioversion/defibrillation shock to the selected cardioversion/defibrillation electrodes.

Figure 3:
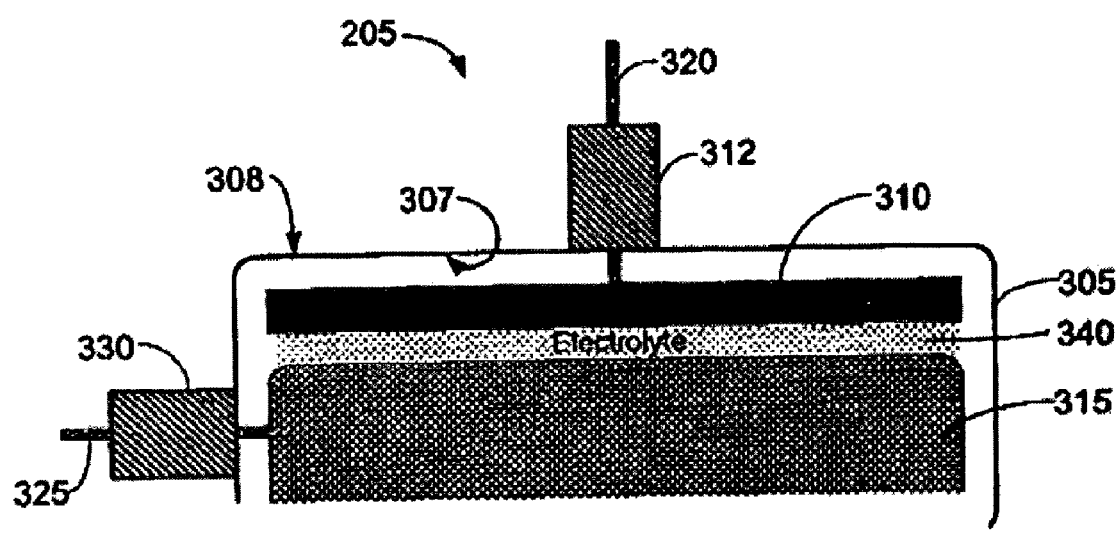
FIG. 3 provides a cross-sectional view of an exemplary capacitor.

Turning now to FIG. 3, a more detailed, cross-sectional view of one of the capacitors 205 that is disposed within the capacitor bank 38 is shown in accordance with one embodiment of the invention. For purposes of clarity and ease in illustrating the present invention, only a portion of the capacitor 205 is shown in FIG. 3. In this particular embodiment, the capacitor 205 includes a hermetically sealed container 305 for encasing the internal contents of the capacitor 205. In accordance with one embodiment, the container 305 is constructed from titanium; however, it will be appreciated that the container 305 may be constructed from various other materials including, but not necessarily limited to, tantalum or niobium without departing from the scope of the invention. The capacitor 205 further comprises a cathode 310, which takes the form of a metal conductive body that is disposed within the container 305. In accordance with an exemplary embodiment, the cathode 310 is separated (i.e., electrically isolated) from an inner surface 307 of the container 305.

The cathode 310 is coupled via an electrical connection to a cathode lead 320 that extends through the inner surface 307 and an outer surface 308 of the container 305. The cathode lead 320 is electrically isolated from the container 305 by a feed-through 312. In one embodiment, the feed-through 312 may be constructed of a glass insulator that seals the cathode lead 320 to the container 305 while maintaining electrical isolation between the cathode lead 320 and the container 305. The feed-through 312, in addition to electrically isolating the cathode lead 320 from the container 305, substantially prevents material, such as a fluid electrolyte, for example, from leaking out of the container 305. The feed-through 312 also substantially prevents foreign substances from entering into the container 305, thus reducing the likelihood of contamination of the container's 305 internal components.

The capacitor 205 is further configured with an anode 315 that is disposed within the container 305. In one embodiment, the anode 315 may be constructed of tantalum. It will be appreciated, however, that the anode 315 may alternatively be constructed of other valve metal materials, such as aluminum, niobium, zirconium, titanium, and alloys including these metals, as well as oxides of these metals. It will also be appreciated that these aforementioned examples of materials used for the anode 315 are not exhaustive. Accordingly, various other conductive materials may be used for the anode 315 in addition to the examples provided above without departing from the scope of the present invention.

The anode 315 is electrically coupled to an anode lead 325 that passes through the inner and outer surfaces 307, 308 of the container 305 via a feed-through 330. The feed-through 330, which may be similar in construction to the feed-through 312 (as previously discussed), electrically isolates the anode lead 325 from the container 305 in substantially the same manner that the feed-through 312 electrically isolates the cathode lead 320 from the container 305.

The container 305 is filled with a fluid electrolyte 340, which is disposed between and in contact with the anode 315 and the cathode 310 of the capacitor 205. The electrolyte 340 provides a current path between the anode 315 and the cathode 310. In accordance with one embodiment, the electrolyte 340 may include a water and glycol ether mixture, phosphoric acid, etc. The selection of the particular electrolyte 340 may depend on the reactivity of the electrolyte 340 with the materials used for the anode 315 and the cathode 310. For example, a sulfuric acid solution used as the electrolyte may be desirable when the anode 315 is composed of tantalum.

Figure 4:
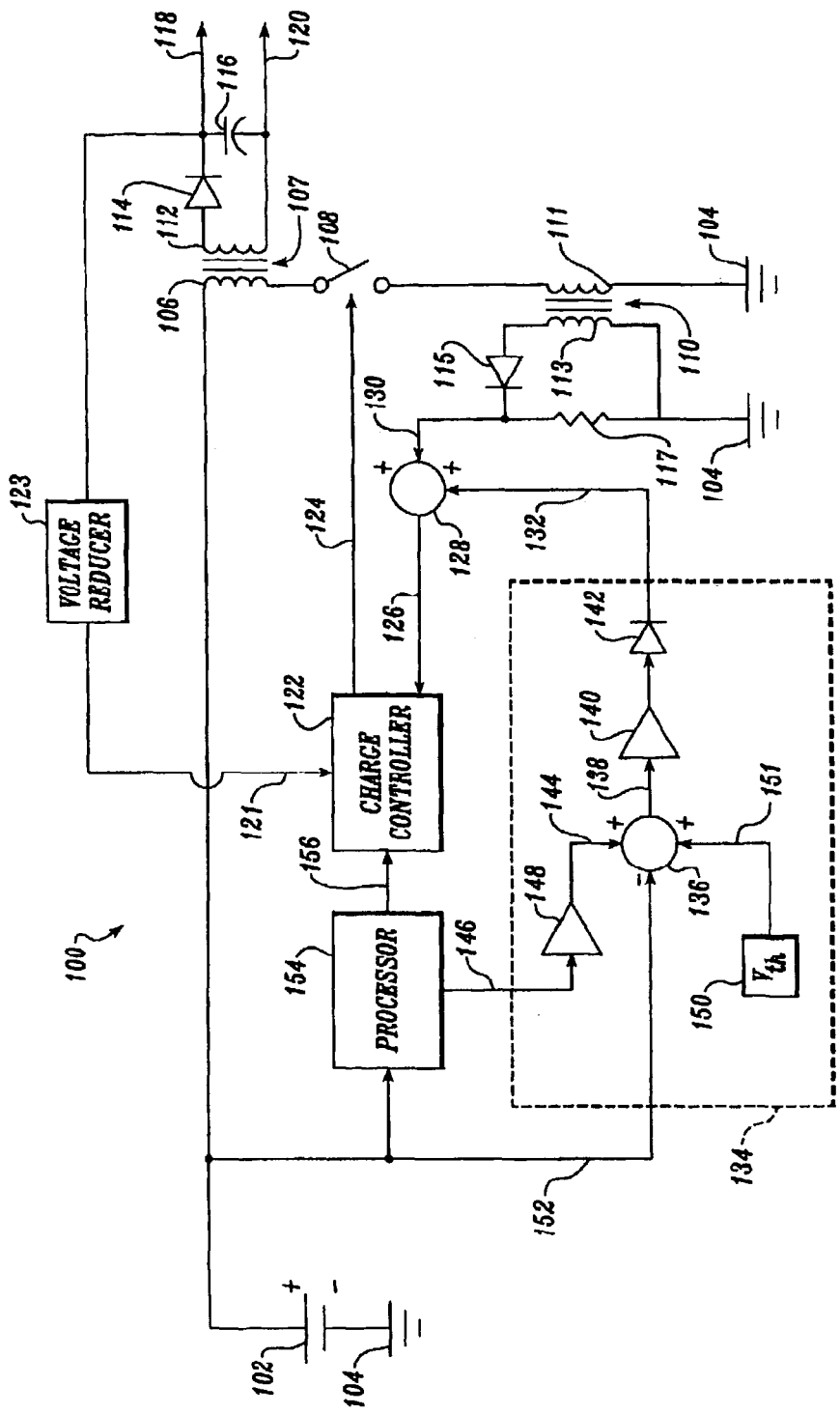
FIG. 4 is an exemplary schematic diagram of a capacitor charging circuit with which the invention may be applied.

FIG. 4 illustrates an exemplary capacitor charging circuit 100 with which the invention may be applied. The capacitor charging circuit 100 charges a capacitor 116 with electrical energy received from a battery 102. A negative terminal of the battery 102 is connected to circuit ground 104, while a positive terminal of the battery 102 is connected to one end of a primary winding 106 of a step-up transformer 107. The other end of the primary winding 106 is connected to a switch 108. When the switch 108 is closed, current drawn from the battery 102 flows through the primary winding 106 and through a current-sense transformer 110 that is connected in series between the switch 108 and circuit ground 104. When the switch 108 is opened, current flow through primary winding 106 and current-sense transformer 110 is interrupted.

The operation of the switch 108 is controlled by a charge controller 122 via a signal applied to a line 124. When the charge controller 122 directs the switch 108 to close, current flows through the primary winding 106, thereby storing energy in the primary winding. When charge controller 122 directs the switch 108 to open, the current flowing through the primary winding 106 is interrupted, causing a transient flyback current to be induced on a secondary winding 112 of the step-up transformer 107. The transient current in the secondary winding 112 is rectified by a diode 114 and applied to the terminals of a high-voltage (energy storage capacitor 116). By cyclically opening and closing the switch 108, currents induced in the secondary winding 112 charge the high-voltage energy storage capacitor 116.

A form of pulse width modulation may be used to govern the cycle in which the switch 108 is opened and closed. Depending on design considerations, "pure" pulse width modulation technology or pulse frequency modulation are suitable for use. In an exemplary embodiment, a hybrid of pure pulse width modulation and pulse frequency modulation is used.

To monitor the charge on the capacitor 116, the charge controller 122 receives a signal over a line 121 from voltage-reducing circuitry 123 that is connected to the capacitor 116. Voltage-reducing circuitry 123 supplies a reduced voltage signal over line 121 in ratio to the voltage charge on capacitor 116, thus enabling the charge controller 122 to determine the degree to which capacitor 116 is charged. Alternatively, the feedback from voltage-reducing circuitry 123 may be directed to a microprocessor 154 after undergoing appropriate analog-to-digital signal conversion. The microprocessor 154 can issue commands to the charge controller 122 via line 156 to control the operation of the charge controller. Defibrillation therapy control circuitry (not shown) connected to the capacitor 116 selectively discharges the capacitor 116 over a pair of lines 118 and 120 and delivers defibrillation therapy to a patient.

Those skilled in the art will appreciate that the switch 108 described above may be implemented using a number of types of solid state devices. Due to the large amount of electrical current that may flow through the switch 108, it is preferred that a transistor be configured to operate as the switch 108. In that case, a "closed" switch refers to a state wherein the transistor allows current to flow through it while an "open" switch refers to a state in which the transistor does not permit current to flow. In many applications, a field effect transistor is suitable for use as the switch 108, wherein the drain and source terminals of the transistor are connected between the primary winding 106 and the current-sense transformer 110, respectively, while the gate terminal is connected to line 124. Depending on the signal applied to the line 124, the switch 108 may permit or interrupt the flow of current through the primary winding 106. The charge controller 122 controls the amount of current flowing through the primary winding 106, and thus controls the rate at which the capacitor 116 is charged, by controlling the cycles in which the switch 108 opens and closes.

Figure 5:
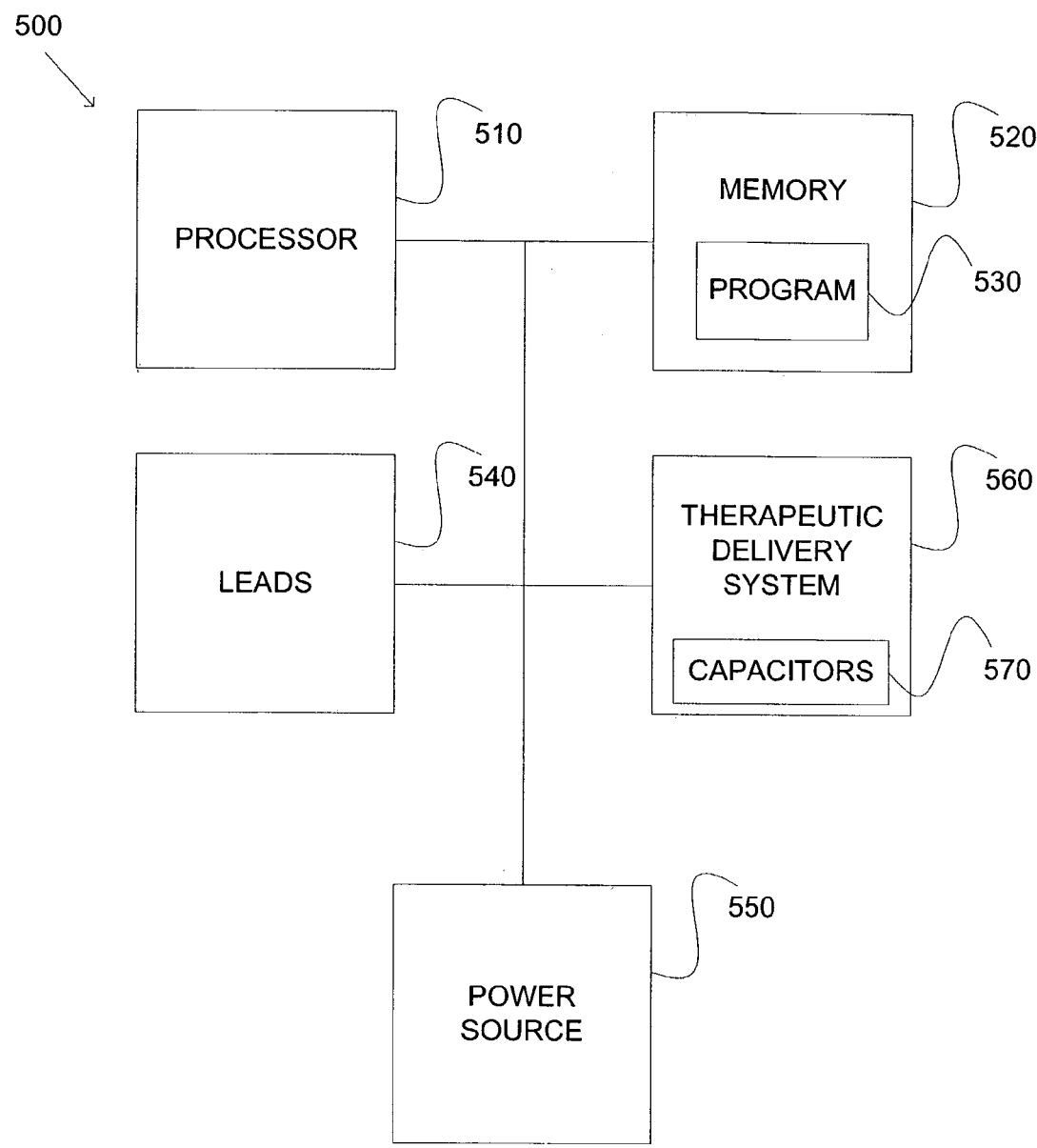
FIG. 5 is an exemplary block diagram of an implantable medical device in the form of a defibrillator.

Referring now to FIG. 5, a generalized system including wet-tantalum capacitors is depicted. System 500 is an exemplary diagram of an ICD. However, although an ICD is depicted in FIG. 5, the invention is not limited to applications in ICDs. ICD 500 includes a processor 510, a memory coupled to the processor 520, the memory having a program 530 residing therein, the program running on processor 510 and providing operation of ICD 500. ICD 500 also includes a plurality of leads 540 which includes at least one electrically conductive lead. The electrically conductive leads may be any of a variety of leads depending on the device, for example, it may be a ventricular or defibrillation lead configured for insertion into the heart. The leads 540 may be used for transmitting therapeutic doses of electrical energy to the heart or further, the leads 540 may be used to sense the behavior of the heart. System 500 also includes a power source 550 that is used to power the electronics of ICD 500 as well as providing power to the therapeutic delivery system 560 which includes circuitry including a series of capacitors 570 and a plurality of supporting electronics (including one or more transformers) for charging and maintaining capacitors 570.

In an exemplary embodiment, capacitors 570 may be an array of wet-tantalum capacitors, possibly, but not limited to, 3 or 4 such wet-tantalum capacitors. According to an exemplary embodiment, each wet-tantalum capacitor includes a metal anode, tantalum oxide ($Ta_2O_5$) dielectric, a liquid electrolyte, and a cathode material.

Figure 6:
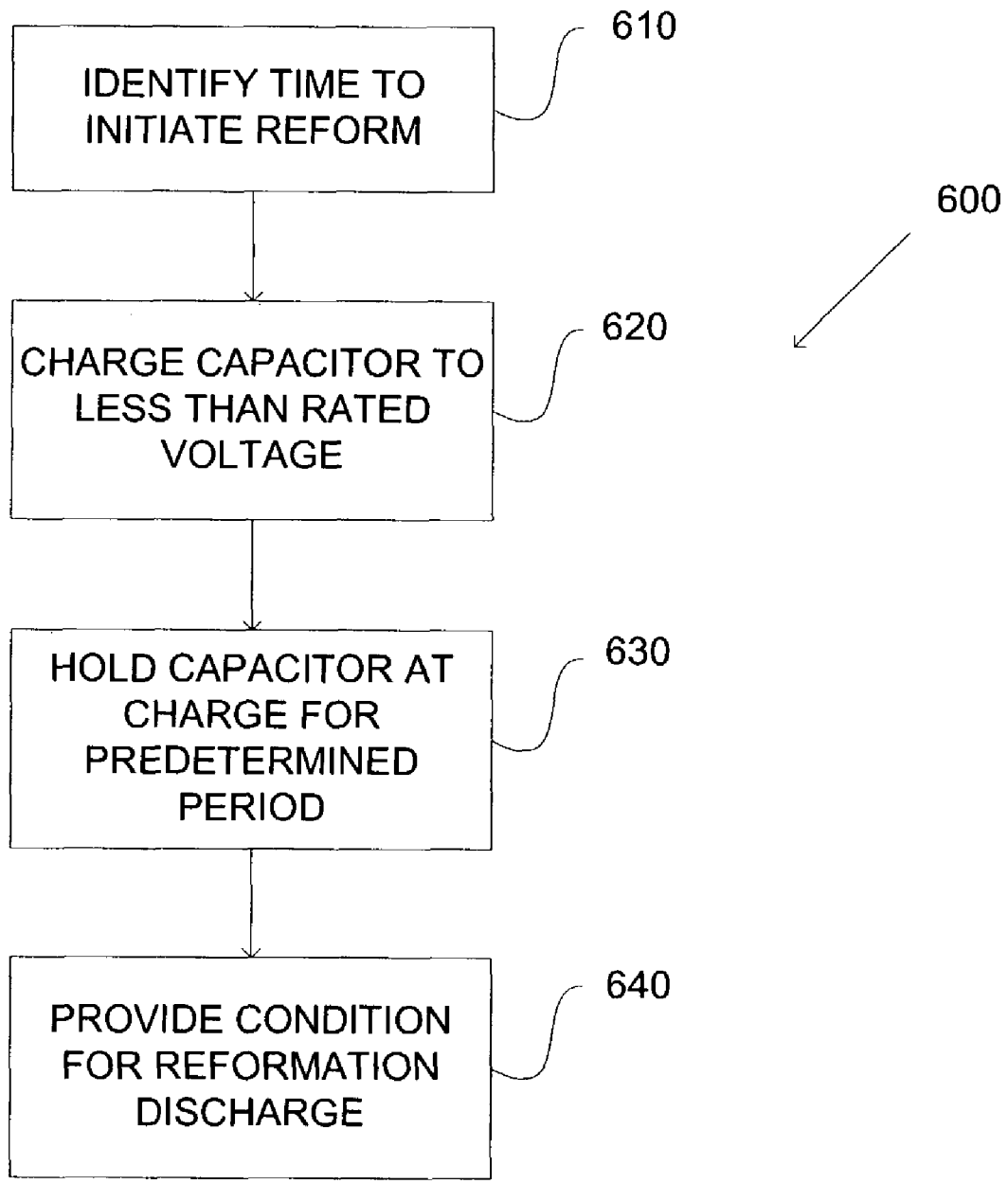
FIG. 6 is an exemplary process diagram for a capacitor reformation process.

Referring now to FIG. 6, a process 600 for reforming wet-tantalum capacitors is depicted. Exemplary process 600 may begin with an identification by the system, a time to initiate the reformation of the capacitor (step 610). Once the reformation is initiated, the capacitor or capacitors are then charged to a voltage that is substantially less than the rated voltage (step 620). In an exemplary embodiment, the rated voltage may be 175, 205, or 215 volts (V) including rated voltages in the range of 150V to 300V, however, capacitors with other rated or maximum voltages may be used.

In general, the reformation process is automatically initiated by the microprocessing device of the IMD. Alternatively, the reformation process may be triggered manually by a clinician, or alternatively, may be triggered remotely through a remote information processing control and communication system.

After a reformation charge cycle, which may be initiated through a slow charging process, has been initiated, a therapeutic discharge cycle may be required during the charging or during other portions of the reformation process. If a therapeutic discharge cycle is initiated, the therapeutic discharge cycle takes precedence over the reformation process and is initiated and carried out to completion or to termination, whichever result is commanded by the microprocessing device. If the therapeutic discharge cycle is initiated, the reformation process may then be delayed or possibly may be reset according to logic within the microprocessing device.

In a particular exemplary embodiment, the charging of the capacitor may be controlled to be charged at a predetermined or closed-loop controlled rate during reformation. The capacitors may be charged at a slow charging rate, compared with the charging rate for therapeutic discharge. The charging rate may be on the order of minutes, hours, or days. Further, the capacitors may be charged to substantially less than the rated voltage. For example, it may be desirable to charge the capacitors to less than 90% of rated voltage or less than 90% of maximum voltage. In another exemplary embodiment, it may be desirable to charge the capacitors to some quantity less than 90% of the rated voltage, for example, it may be desirable to charge the capacitors to any of a range of values under 75% of rated voltage (e.g., 5%, 10%, 15%, 20%, 25%, 50%, etc.). By charging the capacitors to substantially less than the rated voltage or the maximum voltage, the life of the battery is preserved while the efficiency of the reform is believed to be as good or better than prior reformation techniques.

Further, in an exemplary embodiment, the battery may be made smaller if it is not necessary to charge the capacitors all the way to the rated voltage during reformation. Accordingly, space savings in the implantable device, or other device, using the capacitor or capacitor bank result. Once the capacitor is charged to less than the rated voltage (step 620), the capacitor is held at charge for a predetermined period (step 630).

According to an exemplary embodiment, the reformation discharge cycle is initiated immediately after the charging cycle without a holding period. According to other exemplary embodiments, the holding cycle may be a relatively long or relatively short holding cycle on the order of minutes, hours, or days. For example, it may be desirable to hold the charge of the capacitor for 24 hours. During the holding cycle, it also may be desirable to use a top-off circuit and/or process in which the level to which the capacitor was charged initially is held at a constant level during the holding cycle. Absent the top-off circuit, the voltage would drop during the holding period due to leakage currents. Such top-off circuits are well known in the art, however, have not heretofore been applied to the apparatus and method described herein. After the capacitor has been held at charge for a predetermined period (step 630), a condition for reformation discharge is provided (step 640). The discharge may be done through any of a variety of techniques, including discharging through non-therapeutic channels such as but not limited to through a resistance (including a resistor or other resistive load, impedance, etc.). Further, the capacitor may be discharged through an open circuit bleed, that is, through natural leakage current in the system. Typically, if the discharge is through a non-therapeutic load, the discharge may occur relatively rapidly, however, if the discharge is through leakage current, the leakage current will occur over a prolonged period depending on the characteristics of the system.

In an exemplary embodiment, the capacitor is reformed periodically on a schedule, for example, every month, every three months, every six months, etc., or the performance of the capacitor is monitored and the capacitor is reformed according to the sensed condition of the capacitor.

Based on experimental investigations, the deformation mechanism in wet-tantalum capacitors is the result of hydration of either the $Ta_2O_5$ dielectric and/or of a sparingly soluble phosphate deposited within the interstices of the anode during the formation of the anodic oxide. When the capacitor is "fully formed", the phosphate exists in a dehydrated state. As the capacitor rests at open circuit, hydration of the phosphate makes it more conductive, allowing electrical access to more $Ta_2O_5$ surface area. This increases the amount of energy required to charge the capacitor relative to that for a fully formed capacitor.

Reformation of the capacitor, therefore, requires dehydration of the deposit. The dehydration process is assisted by the application of an electric field. The electric field required to provide the dehydration process is relatively low compared to that applied when the capacitor is charged to a high voltage relative to its rated voltage or its maximum-energy voltage. Accordingly, the reformation process, as described above, may be achieved at relatively low voltages. Preferably, the dehydration process, because it is very slow, requires voltage be applied to the capacitors for an extended period. Some benefit may be achieved by applying voltage to the capacitor for several seconds, however, progressively greater reformation is achieved when applying the voltage for greater periods of time, such as minutes, hours, or days. For example, the table provided below shows how providing different reformation voltage levels and discharge techniques produces differing results.

| Capacitor | Fully Formed Charge Energy | Action | Reformation Method | Action | Deformed Charge Energy | Deformation Factor |
|---|---|---|---|---|---|---|
| 1 | 14.2 J | 1-yr. Room Temp. Storage | 110 V charge; 12.5 Ohm discharge | 215 V charge; 12.5 Ohm discharge | 16.0 J | 1.13 |
| 2 | 14.6 J | 1-yr. Room Temp. Storage | 110 V charge; 24 h open circuit bleed; 12.5 Ohm discharge | 215 V charge; 24 h open circuit bleed; 12.5 Ohm discharge | 15.3 J | 1.05 |
| 3 | 14.4 J | 1-yr. Room Temp. Storage | 110 V charge; 5 min. hold at 110 V; 12.5 Ohm discharge | 215 V charge; 5 min. hold at 110 V; 12.5 Ohm discharge | 16.0 J | 1.12 |
| 4 | 14.4 J | 1-yr. Room Temp. Storage | None | 215 V charge; 12.5 Ohm discharge | 16.3 J | 1.13 |

For example, referring to the first line of the table, a first capacitor has a fully formed charge energy of 14.2 J. This is the energy required to fully charge the capacitor in its best performing state. The capacitor no. 1 was then stored at room temperature for one (1) year. During this time, the phosphate became hydrated. The capacitor was then charged to 110V and then discharged through a 12.5 Ohm resistance. Next, the capacitor was then charged to 215V, its rated voltage, and discharged through a 12.5 Ohm discharge which was to simulate a therapeutic discharge. The deformed charge energy is the energy it took to charge the capacitor to the 215V level which provides a deformation factor that is the ratio of the deformed charge energy to the fully formed charge energy of approximately 1.13, therefore, approximately 13% additional energy was required after reformation. In comparison, capacitor 2 shows that a reformation using 110V charge, a 24 hour open circuit bleed, and a 12.5 Ohm discharge followed by a 215V charge, a 24 hour open circuit bleed, and a 12.5 Ohm discharge resulted in a deformation factor of 1.05 which is only about 5% additional energy required.

The improved processes discussed above produce results having certain advantages. Because the capacitor is charged to a relatively low voltage, there is little or no damage to the capacitor, and the capacitor does not exhibit a decrease in service life. Also, because the amount of battery energy expended reforming the capacitor is roughly proportional to the square of the voltage to which the capacitor is charged, the process of reforming at substantially less than the rated voltage consumes much less battery capacity, thereby extending the life of the implantable device, or allowing its size to be reduced. In a typical ICD, the potential longevity increase would be approximately one (1) year, while the potential volume savings may be approximately one (1) cubic centimeter.

A variety of processes may be used depending on the capacitors used to provide these benefits, among others. For example, manual or automatic reformation may be carried out by rapidly or slowly charging the capacitors to a voltage which is not high relative to its rated voltage or maximum-energy voltage. A manual or automatic reformation may be provided for wet-tantalum capacitors by charging them to a voltage which is not high relative to the rated voltage or maximum-energy voltage and holding the capacitor at that voltage for a time before discharging it through a non-therapeutic load. A manual or automatic reformation process for wet-tantalum capacitors may be provided by charging the capacitors to a voltage which is not high relative to their rated voltages or maximum-energy voltages and holding the capacitors at that voltage for a time before allowing them to discharge through internal leakage. Manual or automatic reformation of wet-tantalum capacitors may be provided by charging them to a voltage which is not high relative to their rated voltages or maximum-energy voltages and allowing the capacitors to discharge through internal leakage. Manual or automatic reformation of wet-tantalum capacitors may be provided by charging them to a voltage which is not high relative to their rated voltages or maximum-energy voltages and allowing the capacitor to discharge during internal leakage for a time before discharging them through a non-therapeutic load.

The reformation process described above may be used for a variety of devices not limited to implantable medical devices. The reformation techniques described may be applied to any of a variety of wet-tantalum capacitors used in any electronic devices such as for military applications including munitions, automated external defibrillators (AEDs), as described in U.S. Pat. No. 5,999,852, herein incorporated by reference, photo-flashes, or any other devices in which wet-tantalum capacitors could be applied. Consequently, this invention is not limited to implantable medical devices, but rather extends to any device which utilizes a capacitor requiring reformation. Further, the processes described above may be applicable to other types of capacitors not limited to wet-tantalum capacitors, but other types of capacitors in which the dielectric used and/or phosphate residue deposited within the interstices of the anode during formation of the anodic oxide may become hydrated over time and the application of an electric field may cause dehydration of the dielectric and/or the phosphate and, therefore, provide reformation of the capacitor.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

While the detailed drawings, specific examples and particular formulations given describe preferred and exemplary embodiments, they serve the purpose of illustration only. The inventions disclosed are not limited to the specific forms shown. For example, the methods may be performed in any of a variety of sequence of steps. The hardware and software configurations shown and described may differ depending on the chosen performance characteristics and physical characteristics of the medical devices. For example, the type of medical device or processor used may differ. The systems and methods depicted and described are not limited to the precise details and conditions disclosed. Furthermore, other substitutions, modifications, changes, and omissions may be made in the design, operating conditions, and arrangement of the exemplary embodiments without departing from the scope of the invention as expressed in the appended claims.

What is claimed is:

1. An apparatus for reforming a wet-tantalum capacitor for an implantable medical device, the wet-tantalum capacitor having a hydrated anodic deposit, the apparatus comprising:
 a means for charging the capacitor at a voltage that is no more than seventy-five percent of a rated voltage for the capacitor such that reformation occurs through dehydration of the anodic deposit; and
 a means for providing a condition by which the capacitor is discharged.

2. The apparatus of claim 1, wherein the means for charging the capacitor charges the capacitor automatically.

3. The apparatus of claim 1, wherein the means for charging the capacitor charges the capacitor periodically.

4. The apparatus of claim 1, wherein the means for charging the capacitor holds the capacitor at the voltage for a time period.

5. The apparatus of claim 1, wherein the means for providing a condition by which the capacitor is discharged discharges the capacitor through a non-therapeutic load.

6. The apparatus of claim 1, wherein the means for providing a condition by which the capacitor is discharged discharges the capacitor through a leakage current.

7. The apparatus of claim 1, wherein the voltage is at most approximately seventy percent (70%) of the rated voltage.

8. The apparatus of claim 1, wherein the voltage is at most approximately fifty percent (50%) of the rated voltage.

9. The apparatus of claim 1, wherein the voltage is at most approximately twenty percent (20%) of the rated voltage.

10. The apparatus of claim 1, wherein the means for charging the capacitor charges the capacitor at a substantially slower rate than a nominal therapy charging rate.

11. The apparatus of claim 1, wherein the apparatus causes dehydration of an anodic oxide phosphate deposit.

12. The apparatus of claim 1, wherein the anodic oxide comprises $Ta_2O_5$.

13. The apparatus of claim 11, wherein the phosphate deposit exists in the interstices of the anodic oxide.

14. The apparatus of claim 1, wherein the apparatus comprises a processor for carrying out instructions to charge the capacitor to the voltage and to discharge the capacitor.

15. The apparatus of claim 1, wherein the capacitor has a rated voltage of between approximately 150 and 300 Volts.

16. A method of reforming a wet-tantalum capacitor for an implantable medical device, comprising:
 charging the capacitor at a voltage that is less than approximately seventy-five percent of a rated voltage for the capacitor for an amount of time sufficient to reform the capacitor; and
 providing an open circuit condition and allowing the capacitor to at least partially discharge through leakage current.

17. The method of claim 16, wherein the step of charging the capacitor acts to reform the capacitor through dehydration of an anodic deposit.

18. The method of claim 17, wherein the anodic deposit comprises phosphate.

19. The method of claim 18, wherein the anodic deposit exists in the interstices of an anodic oxide.

20. The method of claim 19, wherein the anodic oxide comprises $Ta_2O_5$.

21. The method of claim 16, further comprising discharging the capacitor through a non-therapeutic load.

22. The method of claim 16, wherein the voltage is less than approximately seventy percent of the rated voltage for the capacitor.

23. The method of claim 16, wherein the voltage is less than approximately fifty percent of the rated voltage for the capacitor.

24. The method of claim 16, wherein the voltage is less than approximately twenty percent of the rated voltage for the capacitor.

25. The method of claim 16, wherein the charging is at a substantially slower rate than a nominal therapy charging rate.

26. A method of reforming a wet-tantalum capacitor for an implantable medical device where the wet-tantalum capacitor includes a hydrated anodic deposit, comprising:
 holding the capacitor at a voltage that is less than approximately seventy-five percent of a rated voltage for the capacitor such that the anodic deposit is dehydrated and the capacitor is reformed; and
 discharging the capacitor through a non-therapeutic load.

27. The method of claim 26, wherein the anodic deposit comprises phosphate.

28. The method of claim 26, wherein the anodic deposit exists in the interstices of an anodic oxide.

29. The method of claim 28, wherein the anodic oxide comprises $Ta_2O_5$.

30. The method of claim 26, further comprising discharging the capacitor through a leakage current.

31. The method of claim 26, wherein the voltage is less than approximately seventy percent of the rated voltage for the capacitor.

32. The method of claim 26, wherein the voltage is less than approximately fifty percent of the rated voltage for the capacitor.

33. The method of claim 26, wherein the voltage is less than approximately twenty percent of the rated voltage for the capacitor.

34. A method of reforming a wet-tantalum capacitor for an implantable medical device, the wet-tantalum capacitor including an anodic oxide phosphate deposit, the method comprising:
 applying an electric field across the capacitor dielectric at a voltage that is less than seventy-five percent of a rated voltage for the capacitor for a sufficient amount of time to reform the capacitor through dehydration of the anodic oxide phosphate deposit.

35. The method of claim 34, wherein the anodic oxide comprises $Ta_2O_5$.

36. The method of claim 35, wherein the phosphate deposit exists in the interstices of the anodic oxide.

37. The method of claim 34, wherein the voltage is less than approximately seventy percent of the rated voltage for the capacitor.

38. The method of claim 34, wherein the voltage is less than approximately fifty percent of the rated voltage for the capacitor.

39. The method of claim 34, wherein the voltage is less than approximately twenty percent of the rated voltage for the capacitor.

\* \* \* \* \*